United States Patent [19]

Robertson

[11] Patent Number: 4,684,748

[45] Date of Patent: Aug. 4, 1987

[54] ANTICONVULSANT AGENTS

[75] Inventor: David W. Robertson, Greenwood, Ind.

[73] Assignee: Eli Lilly and Company, Indianapolis, Ind.

[21] Appl. No.: 759,219

[22] Filed: Jul. 26, 1985

[51] Int. Cl.$^4$ .................. A61K 31/165; C07C 103/82; C07C 103/76

[52] U.S. Cl. .................................... 514/619; 564/166; 564/168

[58] Field of Search ................ 564/166, 168; 514/619

[56] References Cited

U.S. PATENT DOCUMENTS

| | | | |
|---|---|---|---|
| 2,069,740 | 11/1937 | Fleischhauer et al. | 564/168 X |
| 3,008,950 | 11/1961 | Heyna et al. | 564/168 X |
| 4,004,029 | 1/1977 | Collins et al. | 424/325 |
| 4,269,769 | 5/1981 | Moiso et al. | 564/168 X |
| 4,379,165 | 4/1983 | Clark | 424/324 |
| 4,638,014 | 1/1987 | Clark | 514/619 |

OTHER PUBLICATIONS

Grammaticakis, *Compt. Rend.*, 259(23), 4295 (1964) (English Abstract Chemical Abstracts 62:11732b (1965)).
Thiele, Chemical Abstracts 75:35466g (1971).
Thiele, Chemical Abstracts 73:87659a (1970).
Chemical Abstracts 76:140260d (1972).
Dimroth et al., Chemical Abstracts 83:12187t (1975).
Moffett et al., *J. Med. Chem.*, 14(10), 963 (1971).

*Primary Examiner*—Charles F. Warren
*Assistant Examiner*—Carolyn S. Greason
*Attorney, Agent, or Firm*—Robert A. Conrad; Leroy Whitaker

[57] ABSTRACT

This invention provides certain benzamide derivatives, their pharmaceutical formulations, and their use as anticonvulsant agents.

9 Claims, No Drawings

ANTICONVULSANT AGENTS

BACKGROUND OF THE INVENTION

The several anticonvulsant drugs marketed in the United States provide significant seizure relief for only 50–75% of epileptic patients. The therapeutic effects are sometimes accompanied by serious side effects such as sedation, ataxia, psychoses, suicidal depression, gastrointestinal disturbances, gingival hyperplasia, lymphadenopathies, megaloblastic anemias, hepatotoxicity, nephropathies, hirsutism, and fetal malformations. These side effects, which range in severity from mild sedation to death from aplastic anemia, are particularly troublesome since most of the marketed anticonvulsants have very low therapeutic ratios. For example, phenytoin, one of the most widely used anticonvulsants, controls seizures in man only when plasma levels reach 10 mcg/ml. Toxic effects such as nystagmus are seen at around 20 mcg/ml, ataxia is obvious at 30 mcg/ml, and lethargy is apparent at about 40 mcg/ml. See "The Pharmacological Basis of Therapeutics" (Gilman, Goodman, and Gilman, ed., 6th Ed., MacMillan Publishing Co., Inc., New York, N.Y. (1980)), p. 455. In view of these facts, most epileptologists indicate there is a definite need for more selective and less toxic anticonvulsant drugs.

SUMMARY OF THE INVENTION

This invention provides p-aminobenzamides of the formula I

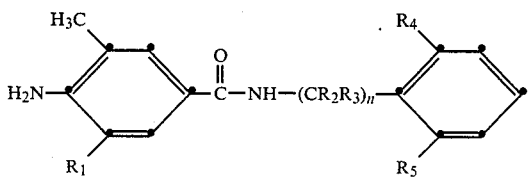

wherein $R_1$, $R_2$, $R_3$, $R_4$, and $R_5$ are each independently hydrogen or methyl; and n is 0 or 1; and pharmaceutically acceptable acid addition salts thereof.

This invention also provides a method for treating and preventing convulsions in mammals in need of such treatment which comprises administering to said mammal an effective amount of a compound as defined above.

According to a further aspect of the present invention, there are provided pharmaceutical formulations which comprise an active ingredient a benzamide of formula I in association with a pharmaceutically acceptable carrier or diluent.

This invention also provides compounds of the formula II

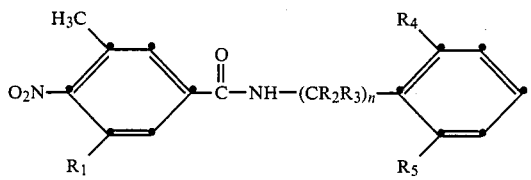

wherein $R_1$, $R_2$, $R_3$, $R_4$, $R_5$, and n are the same as previously defined. These nitro derivatives are useful as intermediates for preparing the anticonvulsant p-aminobenzamides of formula I.

DETAILED DESCRIPTION AND PREFERRED EMBODIMENT

The present invention relates to organic compounds that are useful for treating and preventing convulsions in mammals.

The preferred compounds of this invention are those wherein n is 0 and at least one of $R_4$ and $R_5$ is methyl. Alternatively, when n is 1, it is preferred that at least one of $R_2$ and $R_3$ is methyl and that $R_4$ and $R_5$ are each hydrogen.

The pharmaceutically acceptable acid addition salts of this invention can be prepared by standard methods known in the art employing those acids of sufficient acidity to form acid addition salts with the basic aniline group. These include salts derived from inorganic acids such as hydrochloric acid, nitric acid, phosphoric acid, sulfuric acid, hydrobromic acid, hydriodic acid, phosphorous acid and the like, as well as salts derived from organic acids such as aliphatic mono- and di-carboxylic acids, phenyl-substituted alkanoic acids, hydroxyalkanoic and -alkanedioic acids, aromatic acids, aliphatic and aromatic sulfonic acids, etc. Such pharmaceutically acceptable salts thus include sulfate, metaphosphate, pyrophosphate, chloride, bromide, iodide, fluoride, oxalate, maleate, benzenesulfonate, toluenesulfonate, chlorobenzenesulfonate, methanesulfonate, propanesulfonate, naphthalene-1-sulfonate, naphthalene-2-sulfonate and the like. The Preferred salts are those derived from inorganic acids, especially hydrochloric acid.

The compounds of formula I may be prepared by any of several methods well known in the art. A preferred method comprises reacting a p-nitrobenzoyl halide III with an amine IV according to the general method as taught in U.S. Pat. No. 4,379,165, and according to the following scheme:

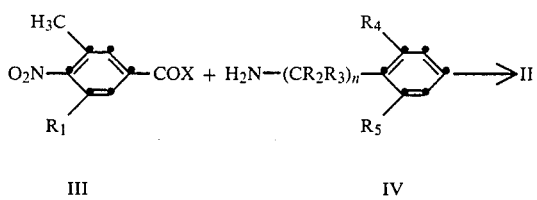

wherein

X is a leaving group such as $C_1$–$C_3$ alkoxy or halo, especially chloro. The reaction follows the general procedure of reaction A in the above mentioned patent. It is preferred that a benzoyl halide and he amine be reacted in a non-reactive solvent, such as tetrahydrofuran, preferably in the presence of an acid scavenger such as a carbonate, especially potassium carbonate, or an organic base, such as triethylamine. Although it is preferred that the reactants be added in molar ratios of about 1.5:1.0 (III:IV), other ratios are completely operative. The reaction is carried out from about room temperature up to the reflux temperature of the reaction mixture. Under the preferred conditions of reflux, the reaction is generally complete in 1–12 hours.

The p-nitrobenzamides of the invention may be converted into the corresponding p-aminobenzamides by any of a number of reductive methods. The preferred procedure is the hydrogenation procedure which may be identical with or equivalent to the conditions taught as reaction B in the above patent. Generally, the p-nitrobenzamide is hydrogenated under low pressure in a non-reactive solvent such as an alcohol, especially ethanol, in the presence of a catalyst, such as palladium on charcoal. The reaction is generally complete in about 2-4 hours.

The individual enantiomers of this invention may be prepared from the racemate (i.e., when n is 1, one of $R_2$ and $R_3$ is hydrogen and the other of $R_2$ and $R_3$ is methyl) by standard methods of isomeric resolution known in the art, such as crystallization, salt formation, high pressure liquid chromatography, etc. In addition, the enantiomers can be prepared by resolving the intermediate p-nitrobenzamide in the same manner and then hydrogenating the individual isomers in the usual way. However, the preferred method of preparing the enantiomers of this invention comprises reacting a p-nitrobenzoyl halide with enantiomerically pure amine followed by reduction.

Alternatively, the p-nitrobenzamide intermediates of formula II may be prepared, for example, from p-nitrobenzoic acid ester derivatives of III (e.g., where X is $OCH_3$) upon reaction with IV. This aminolysis reaction is generally known and is preferably accomplished by heating the two reactants in a non-reactive solvent such as an alcohol, at temperatures from about 40°-100° C. Anhydrides of p-nitrobenzoic acid may also be employed in the reaction with the amines of Formula IV. In addition, p-nitrobenzoic acid may be reacted with the required amine in the presence of coupling reagents such as DCC, EEDQ, CDI, etc.

The intermediates of Formulas III and IV and other necessary reagents are commercially available, are known in the art, or can be prepared by methods taught in the literature.

The p-aminobenzamides of this invention are anticonvulsant agents and may be administered by various routes including the oral, rectal, transdermal, subcutaneous, intravenous, intramuscular, or intranasal routes, being usually employed in the form of a pharmaceutical composition. It is a special feature of these compounds that they are effective following oral administration. The invention includes a pharmaceutical composition comprising from about 1% to about 95% by weight of a p-aminobenzamide of Formula I, or a pharmaceutically acceptable acid addition salt thereof, associated with a pharmaceutically acceptable carrier.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions are preferably formulated in a unit dosage form, each dosage containing from about 5 to 500 mg, more usually 25 to 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

The active compounds are effective over a wide dosage range. For example, dosages per day will normally fall within the range of about 0.5 to 300 mg/kg of body weight. In the treatment of adult humans, the range of about 1 to 50 mg/kg, in single or divided doses, is preferred. However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms.

The following examples further illustrate the preparation of the intermediates, compounds, and formulations of this invention. The examples are illustrative only and are not intended to limit the scope of the invention in any way.

EXAMPLE 1

3,5-Dimethyl-N-[(2-methylphenyl)methyl]-4-nitrobenzamide

A solution of 3,5-dimethyl-4-nitrobenzoyl chloride in tetrahyrofuran, generated from 7.0 g of 3,5-dimethyl-4-nitrobenzoic acid by standard procedures, was added to 4.3 g of 2-methylbenzyl amine and 5.0 ml of triethylamine in tetrahydrofuran. The reaction was stirred at ambient temperature overnight, chilled, and filtered. The filtrate was evaporated in vacuo and the residue therefrom was dissolved in chloroform, washed sequentially with 1N hydrochloric acid, 1N sodium hydroxide, water, and a saturated sodium chloride solution, dried over sodium sulfate, filtered, and evaporated in vacuo. Crystallization from methanol/water provided 4.7 g of the desired title product, m.p. 202°-203° C.

Analysis for $C_{17}H_{18}N_2O_3$: Calculated: C, 68.44; H, 6.08; N, 9.39; Found: C, 68.28; H, 6.01; N, 9.43.

EXAMPLES 2-11

The following intermediates were prepared from the appropriate acid chloride and corresponding amine according to the procedure of Example 1.

2. N-(2,6-dimethylphenyl)-3-methyl-4-nitrobenzamide, 49% yield, m.p. 175°-177° C.

Analysis for $C_{16}H_{16}N_2O_3$: Calculated: C, 67.59; H, 5.67; N, 9.85; Found: C, 67.48; H, 5.54; N, 9.69.

3. 3,5-Dimethyl-4-nitro-N-(2,6-dimethylphenyl)benzamide, 65% yield, m.p. 250°-252° C.

Analysis for $C_{17}H_{18}N_2O_3$: Calculated: C, 68.44; H, 6.08; N, 9.39; Found: C, 68.44; H, 5.92; N, 9.11.

4. (R,S)-3-methyl-4-nitro-N-(1-phenylethyl)benzamide, 100% yield.

5. 3-Methyl-4-nitro-N-(2-methylphenyl)benzamide, 32% yield, m.p. 154°–156° C.

Analysis for $C_{15}H_{14}N_2O_3$: Calculated: C, 66.66; H, 5.22; N, 10.36; Found: C, 66.90; H, 5.45; N, 10.29.

6. 3,5-Dimethyl-4-nitro-N-benzylbenzamide, 89% yield, m.p. 127°–129° C.

Analysis for $C_{16}H_{16}N_2O_3$: Calculated: C, 67.59; H, 5.67; N, 9.85; Found: C, 67.64; H, 5.67; N, 9.67.

7. 3-Methyl-N-[(2-methylphenyl)methyl]-4-nitrobenzamide, 94% yield, m.p. 134°–135° C.

Analysis for $C_{16}H_{16}N_2O_3$: Calculated: C, 67.59; H, 5.67; N, 9.85; Found: C, 67.71; H, 5.79; N, 10.03.

8. 3-Methyl-4-nitro-N-benzylbenzamide, 91% yield, m.p. 84°–85° C.

Analysis for $C_{15}H_{14}N_2O_3$: Calculated: C, 66.66; H, 5.22; N, 10.36; Found: C, 66.69; H, 5.44; N, 10.14.

9. (R)-3,5-dimethyl-4-nitro-N-(1-phenylethyl)benzamide, 70% yield. The proton NMR and mass spectra were consistent with the structure of the desired product.

10. (S)-3,5-dimethyl-4-nitro-N-(1-phenylethyl)benzamide, 49% yield. The proton NMR and mass spectra were consistent with the structure of the desired product.

11. (R,S)-3,5-dimethyl-4-nitro-N-(1-phenylethyl)benzamide, 44% yield, m.p. 150°–152° C.

Analysis for $C_{17}H_{18}N_2O_3$: Calculated: C, 68.44; H, 6.08; N, 9.39; Found: C, 68.16; H, 5.99; N, 9.30.

EXAMPLE 12

(R,S)-4-amino-3-methyl-N-(1-phenylethyl)benzamide hydrochloride

A solution of 7.5 g of (R,S)-3-methyl-4-nitro-N-(1-phenylethyl)benzamide in 200 ml of ethanol/tetrahydrofuran was hydrogenated over 5% palladium on carbon. After the theoretical amount of hydrogen was consumed, the mixture was filtered and the filtrate evaporated. The residue was dissolved in a small volume of ethanol, approximately 1.5 molar equivalents of concentrated hydrochloric acid were added, and diethyl ether was added until cloudy. After standing overnight, 6.1 g of the title product were recovered by filtration, m.p. 200°–201° C.

Analysis for $C_{16}H_{17}N_2O \cdot HCl$: Calculated: C, 66.32; H, 6.26; N, 9.67; Cl, 12.23; Found: C, 66.52; H, 6.36; N, 9.76; Cl, 11.97.

EXAMPLES 13–21

The following compounds were prepared by the method of Example 12 from the corresponding nitro intermediates previously described.

13. 4-Amino-3,5-dimethyl-N-[(2-methylphenyl)methyl]benzamide, 90% yield, m.p. 160°–161.5° C.

Analysis for $C_{17}H_{20}N_2O$: Calculated: C, 76.09; H, 7.51; N, 10.44; Found: C, 75.83; H, 7.29; N, 10.23.

14. 4-Amino-N-(2,6-dimethylphenyl)-3-methylbenzamide, 70% yield, m.p. 269°–270° C.

Analysis for $C_{16}H_{18}N_2O$:

Calculated: C, 75.56; H, 7.13; N, 11.01; Found: C, 75.31; H, 6.95; N, 10.73.

15. 4-Amino-N-(2,6-dimethylphenyl)-3,5-dimethylbenzamide, 80% yield, m.p. 167°–169° C.

Analysis for $C_{17}H_{20}N_2O$: Calculated: C, 76.09; H, 7.51; N, 10.44; Found: C, 75.87; H, 7.28; N, 10.28.

16. 4-Amino-3-methyl-N-(2-methylphenyl)benzamide, 84% yield, m.p. 183°–184° C.

Analysis for $C_{15}H_{16}N_2O$: Calculated: C, 74.97; H, 6.71; N, 11.66; Found: C, 74.68; H, 6.64; N, 11.54.

17. 4-Amino-3,5-dimethyl-N-benzylbenzamide, 82% yield, 124°–125° C.

Analysis for $C_{16}H_{18}N_2O$: Calculated: C, 75.56; H, 7.13; N, 11.01; Found: C, 75.48; H, 7.03; N, 10.88.

18. 4-Amino-3-methyl-N-(2-methylbenzyl)benzamide, 93% yield, m.p. 131°–133° C.

Analysis for $C_{16}H_{18}N_2O$: Calculated: C, 75.56; H, 7.13; N, 11.01; Found: C, 75.28; H, 6.87; N, 11.18.

19. 4-Amino-3-methyl-N-benzylbenzamide hydrochloride, 79% yield, m.p. 240°–241° C.

Analysis for $C_{15}H_{17}N_2O \cdot HCl$: Calculated: C, 65.10; H, 6.19; N, 10.12; Found: C, 64.16; H, 5.68; N, 10.43.

20. (R)-4-amino-3,5-dimethyl-N-(1-phenylethyl)benzamide, 60% yield, m.p. 226°–227° C.

Analysis for $C_{17}H_{20}N_2O$: Calculated: C, 76.09; H, 7.51; N, 10.44; Found: C, 76.37; H, 7.53; N, 10.22.

21. (S)-4-amino-3,5-dimethyl-N-(1-phenylethyl)benzamide, 78% yield, m.p. 226°–227° C.

Analysis for $C_{17}H_{20}N_2O$: Calculated: C, 76.09; H, 7.51; N, 10.44; Found: C, 76.30; H, 7.77; N, 10.19.

EXAMPLE 22

(R,S)-4-amino-3,5-dimethyl-N-(1-phenylethyl)benzamide

A solution of 5.0 g of (R,S)-3,5-dimethyl-4-nitro-N-(1-phenylethyl)benzamide in 50 ml of glacial acetic acid was added dropwise to a boiling slurry of 14.7 g of iron powder in 100 ml of ethanol. The mixture was heated at reflux for two hours, cooled to ambient temperature, and filtered. The filtrate was evaporated in vacuo and the residue was partitioned between ethyl acetate and a 10% aqueous sodium bicarbonate solution. The organic layer was separated, washed with water and a saturated sodium chloride solution, dried over sodium sulfate, and evaporated in vacuo. The residue was purified by chromatography over silica gel followed by crystallization from water/methanol to provide 1.5 g of the title product, m.p. 194°–195° C.

Analysis for $C_{17}H_{20}N_2O$: Calculated: C, 76.09; H, 7.51; N, 10.44; Found: C, 76.05; H, 7.50; N, 10.28.

The following formulation examples may employ as active compounds any of the pharmaceutical compounds of the invention of their pharmaceutically acceptable salts.

EXAMPLE 23

Hard gelatin capsules are prepared using the following ingredients:

|  | Quantity (mg/capsule) |
|---|---|
| 4-Amino-3,5-dimethyl-N—benzylbenzamide sulfate | 250 |
| Starch dried | 200 |
| Magnesium stearate | 10 |

The above ingredients are mixed and filled into hard gelatin capsules in 460 mg. quantities.

EXAMPLE 24

A tablet formula is prepared using the ingredients below:

|  | Quantity (mg/tablet) |
| --- | --- |
| 4-Amino-3,5-dimethyl-N—(2,6-dimethylphenyl)benzamide hydrobromide | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 25

An aerosol solution is prepared containing the following components:

|  | Weight % |
| --- | --- |
| (R)-4-Amino-3-methyl-N—(α,α-dimethylbenzyl)benzamide hydrochloride | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

EXAMPLE 26

Tablets each containing 60 mg of active ingredient are made up as follows:

| 4-Amino-3,5-dimethyl-N—(2,6-dimethylphenyl)benzamide | 60 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 27

Capsules each containing 80 mg of medicament are made as follows:

| 4-Amino-3-methyl-N—[1-(2,6-dimethylphenyl)ethyl]benzamide | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 28

Suppositories each containing 225 mg of active ingredient are made as follows:

| 4-Amino-3,5-dimethyl-N—(2-methylbenzyl)benzamide | 225 mg |
| --- | --- |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 29

Suspensions each containing 50 mg of medicament per 5 ml dose are made as follows:

| 4-Amino-3,5-dimethyl-N—(α,α,2,6-tetramethylbenzyl)benzamide hydrochloride | 50 mg |
| --- | --- |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

. The compounds of Formula I are anticonvulsant agents with a high therpeutic ratio and long half-life and are therefore useful in the treatment and prevention of convulsions in mammals. Moreover, the anticonvulsant compounds of this invention, in contrast to anticonvulsant benzamides taught in the art, do not cause hemolysis. The compounds are effective against tonic extensor seizures elicited by maximal electroshock and should therefore be useful for treating generalized tonic-clonic ("grand mal"), cortical focal, complex partial (temporal lobe epilepsy), simple partial (focal moor), and post-traumatic seizures in humans. This activity is demonstrated in the electroshock induced convulsion inhibition assay which follows.

In the electroshock induced convulsion inhibition assay (E.S.), the compound to be tested was suspended in acacia and administered by gavage to each of ten Cox standard strain albino male mice (18-24 g) at the dose level being investigated. Thirty to 180 minutes after compound administration, the mice were subjected to a 0.1 second, 50 milliampere electroshock through corneal electrodes. The animals were examined and evaluated immediately after the electroshock for the occurrence of clonic, flexor tonic, or extensor tonic convulsions, or death and the $ED_{50}$ was determined for each compound as the dose which inhibited the occurrence of extensor tonic convulsions in one half of the animals immediately after the electroshock. For comparison, 18 milliamperes was usually sufficient to produce extensor tonic convulsions in about half of the control animals; at 50 milliamperes, almost all control animals (receiving vehicle only) died. The test results summarized in Table I are reported as the $ED_{50}$ values at the time interval found to provide an optimal response after dosing.

TABLE I

Anti-convulsant Activity of compounds of Formula I

| Example No. | Electroshock $ED_{50}$ (mg/kg)* | Time After dosing (minutes)** |
| --- | --- | --- |
| 12 | 20.0 | 60 |
| 13 | 20.0 | 60 |
| 14 | 3.8 | 60 |
| 15 | 5.6 | 60 |
| 16 | 5.4 | 30 |
| 17 | 75 | 120 |
| 18 | 16.3 | 60 |
| 19 | 9.6 | 30 |
| 20 | 46.8 | 180 |
| 21 | 60.5 | 180 |
| 22 | 26.7 | 180 |

*oral dose (gavage)-See text for methodology.
**Time (between dosing and administration of the electroshock) providing an optimal response.

I claim:

1. A compound of the Formula

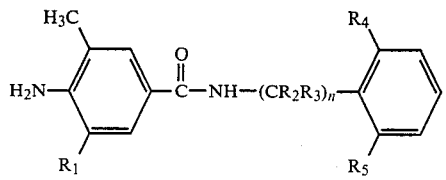

I wherein $R_1$, $R_2$, and $R_3$ are each independently hydrogen or methyl; $R_4$ and $R_5$ are each methyl; and n is 0; and pharmaceutically acceptable acid addition salts thereof.

2. The compound of claim 1 which is 4-amino-3-methyl-N-(2,6-dimethylphenyl)benzamide or a pharmaceutically acceptable acid addition salt thereof.

3. The compound of claim 1 which is 4-amino-3,5-dimethyl-N-(2,6-dimethylphenyl)benzamide or a pharmaceutically acceptable acid addition salt thereof.

4. A pharmaceutical formulation which comprises a compound of claim 1 in association with a pharmaceutically acceptable carrier or diluent.

5. A formulation according to claim 4 employing 4-amino-3-methyl-N-(2,6-dimethylphenyl)benzamide or a pharmaceutically acceptable acid addition salt thereof.

6. A formulation according to claim 4 employing 4-amino-3,5-dimethyl-N-(2,6-dimethylphenyl)benzamide or a pharmaceutically acceptable acid addition salt thereof.

7. A compound of the formula

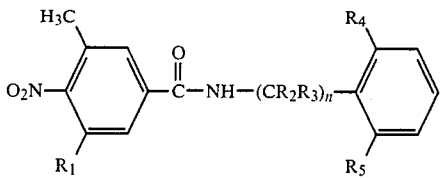

II wherein $R_1$, $R_2$ and $R_3$ are each independently hydrogen or methyl; $R_4$ and $R_5$ are each methyl; and n is 0.

8. The compound of claim 7 which is 3-methyl-4-nitro-N-(2,6-dimethylphenyl)benzamide.

9. The compound of claim 7 which is 3,5-dimethyl-4-nitro-N-(2,6-dimethylphenyl)benzamide.

* * * * *